United States Patent [19]

Penn

[11] 4,029,768

[45] June 14, 1977

[54] COMPOSITION FOR APPLICATION TO THE ANIMAL BRAIN FOR SYNTHESIS OF BRAIN COMPONENTS INVOLVED IN THE LEARNING PROCESS, AND METHOD

[76] Inventor: Nathar W. Penn, 453 Glendale Road, Wyckoff, N.J. 07481

[22] Filed: Mar. 16, 1971

[21] Appl. No.: 124,959

[52] U.S. Cl. .................................................. 424/95
[51] Int. Cl.² ....................................... A61K 35/12
[58] Field of Search ...................... 424/95; 107/65

[56] References Cited
OTHER PUBLICATIONS

Am. J. Psychiatry – Apr. 1958 (p. 943).

*Primary Examiner*—Stanley J. Friedman
*Attorney, Agent, or Firm*—W. Lee Helms

[57] ABSTRACT

A composition for application to the animal brain (this term is used to include both humans and lower animals) for synthesis of brain components involved in the learning process, thereby facilitating learning. The composition comprising brain deoxyribonucleic acid containing 5-hydroxymethyloytosine ranging from about 8 to 15% of the total cytosines present. The invention includes dosage and method of preparation.

2 Claims, No Drawings

COMPOSITION FOR APPLICATION TO THE ANIMAL BRAIN FOR SYNTHESIS OF BRAIN COMPONENTS INVOLVED IN THE LEARNING PROCESS, AND METHOD

METHOD OF PREPARATION

It is postulated that in the practice of the invention, the brain of an animal of the same species, or of a related species, should be the basic source of the composition when applied to a given animal species. For example, for use in application to a rat, a mouse brain is effective, and in terms of use in retarded humans, the chimpansee, monkey, etc. may be postulated as a "related" species within the purview of the invention.

As an example, brains were removed from a plurality of rats and immediately homogenized in a Potter homogenizer, with 10 volumes of solution A, of the following solutions:

| Solutions: | Concentration: | | | | |
|---|---|---|---|---|---|
| | A | B | C | D | E |
| Sidium Bromide | 4.5M | — | — | 2M | — |
| Potassium Citrate, pH 8.6 | .01M | .01M | .01M | .01M | .001M |
| Sodium Arsenate | .01M | .01M | .01M | .01M | — |
| Sodium Arsenite, pH 8.6 | .01M | .01M | .01M | .01M | — |
| Sodium Deoxycholate, phy 8.6 | .04% | .02% | — | .04% | — |
| Glutathione, pH 8.6 | .03M | .03M | .03D .03M | .001M | |
| Sodium Chloride | — | — | — | — | .14M |

After the said homogenizing action, the suspension was centrifuged at 28,000 Xg for 2 minutes. The solution under the floating solid layer was withdrawn and 2 volumes of ethanol were added to it. The precipitate was wrapped on a stirring rod and transferred to solution B. The solid layer, less said precipitate, was extracted again by gentle homogenization with solution A and centrifuged as before. The solution under the floating solid is removed and treated as in the first step. These extractions are continued until no precipitate is obtained which can be wrapped on a stirring rod.

The combined wrapped precipitates are extracted by homogenization in solution B. The suspension is centrifuged as before and a precipitant and supernatant fraction are obtained. The latter is poured off, ethyl alcohol is added and the wrapped precipitate is transferred to solution C. Extraction is continued until no wrapped material is obtained.

The combined solids in solution C are gently homogenized into solution and centrifuged as before. Traces of sediment are extracted with a small amount of solution C, centrifuged, and the solution is combined with the original supernatant fraction of solution C.

A solution of lysozyme, 50 milligrams per milliter at pH 5, is added dropwise, 0.11 milliliter for each milliter of C, with vigorous stirring. The mixture is stirred intermittently during half an hour and centrifuged 3 minutes at 10,000 Xg. The precipitate is washed twice with solution C and centrifuged at 10,000 Xg for 3 minutes each time. The supernatant solutions are discarded.

Solution D is added to the final residue and it is then extracted by the same steps used for solutions A and B, except that centrifugations are carried out at 10,000 Xg for 2 minutes. The wrapped precipitates are placed in fresh solution B. They are homogenized into solution, centrifuged, and traces of sedimented solid re-extracted with a small amount of B. The combined solutions B are shaken by hand with an equal amount of chloroform-isoamyl alcohol solution 24.1, volume to volume. The mixture is centrifuged 15 minutes at 1000 Xg. The aqueous layer is removed and the organic layer shaken again with a small amount of B and centrifuged as before. The aqueous solutions are combined and 2 volumes of ethyl alcohol are added. The wrapped solid is transferred to solution E. It is extracted by homogenization and centrifugation as in Solution D. The aqueous solutions are combined and then precipitated by addition of 2 volumes of ethyl alcohol. The wrapped solid is washed in fresh 65% ethyl alcohol, dried in vacuo at room temperature and stored in vacuo at −15° C over a desicant.

In the above method, the use of Glutathione at the concentration employed inhibits enzymes which otherwise would degrade the product during its recovery; and also Glutathione removes certain fractions which contain phosphorous. Lysozyme is a basic protein which reacts with the acidic groups to form an insoluble complex under certain conditions. Even the highly purified Lysozyme obtained specially from supply houses must be further treated in two steps to remove traces of enzymes and to remove other substances which act upon the Lysozyme itself to destroy or greatly reduce the precipitation of the compound sought. The first step is heating in a boiling water bath (temperature about 95° C) for 20 minutes and the second is extraction with one or more organic solvents.

The precipitate obtained by use of Lysozyme has several unique and useful properties, as follows:

a. It is rapidly formed and readily dissolved by a suitable salt concentration;

b. It can be washed with dilute salt solutions to remove types of impurities such as glycogen and most of the RNA without loss of deoxyribonucleic acid;

c. Determinations of deoxyribonucleic acid in the precipitate can be performed colorimetrically, d. Lysozyme is readily removed by conventional treatment after dissolving the precipitate. It is not precipitated by alcohol (66%) and it also is removed by extraction with a solution of chloroform-isoamyl alcohol.

Arsenite has been used herein (along with Arsenate), for blocking certain energy-yielding reactions and increasing the yield of the compound significantly. Energy yielding reactions in the cell lead to degradation during recovery unless they are inhibited.

The same method was employed with brain obtained from mice and the product obtained was the same, as to the function sough, as will be hereinafter referred to.

EXAMPLES OF DOSAGE

In Example use of the compound obtained from the brains of rats and the related mice, two groups of rats were employed, viz: A group A which received by injection the compound, and a second group B which received none of the compound. Some of the rats in group B were not injected at all, most were injected with other substances. The group B is termed the "Control Group." The rats of the two groups weighed 55–65 grams and may be considered as of the average weight of 60 grams. Thus the average brain weight may be postulated as 1.5 gm.

The dosage per each injected rat ranged from 0.125 to 0.2 milligrams in a solvent selected as sodium chloride + sodium citrate, the solution being kept small, i.e. 0.02–0.03 cc. The compound was directly injected into the lateral ventricle of the brain.

42 hours were allowed to lapse before testing, although no overt effects were observed in the injected rats. On the second day after injection at the beginning of the usual one-half hour feeding time, each animal of the two groups was not given food but instead was transferred to a "Skinner Box," a standard test medium of animal psychologists, and particularly adapted for the tests which followed.

The "Skinner box" employed allows delivery of a small pellet of regular rat food to a shelf in the box, when a bar spaced about two inches from the pellet delivery orifice is depressed. The number of bar depressions is recorded automatically both by a counter, and simultaneously by a pen mark on a continuously moving paper tape, which is marked at zero time and which moves at a constant rate. The time intervals thus can be readily determined. The automatic counter gives the total number of the bar depressions, and serves as a control for the pen-counter, since the total number of marks on the paper tape equals the number recorded by the counter. As stated, food was obtainable only by depressing the bar, to permit one pellet to drop on the shelf.

A plurality of groups A and B were arranged and tested over a period of six weeks. The time of day at which the animals of the groups A and the animals of the groups B were trained and then tested was varied. The possibility was thus excluded that the animals' alertness or activity at a given hour might significantly affect the results. The "training" was given to all of the animals of the groups A and the groups B was the same and consisted of feeding each animal individually at a specific time of day for one-half hour out of each 24 hours, over a period of 3 days. Each animal was then tested at that particular hour of day.

Under the conditions given, all injected animals, of the said groups A learned to obtain food within 15 minutes. All "controls," and hence all of groups B did not learn before 32 minutes or longer. These results are highly significant to animal psychologists. The behaviour of the Groups A differed from the Groups B "controls." The Groups A rats, injected with brain deoxyribonucleic acid, focused their activities in the neighborhood of the delivery shelf, in each case, spending far more time there than the controls with respect to the shelf for each control rat, and until learning occurred. In anthropmorphic terms, the test animals "concentrated," whereas the control animals rapidly showed frustration at their failure to obtain food, and roamed about the box, the contrast in behaviour being impressive.

Injection of the compound into the lateral ventricle of the brain, is desirable since the cerebral hemisphere is in direct contact therewith and is the site of higher learning and correlative functions. As to the dosage for higher animals including man, it may be stated that a proper level is 0.15 to 0.2 milligrams of the composition, per gram of brain tissue in the recipient. The composition preferably is dissolved in a solution of 0.14M sodium chloride and 0.001M sodium citrate, pH 8.6 to give a final concentration of about 3–5 milligrams per cc.

With regard to the above stated tests of use of the compound injected into the brains of groups of rats, as compared with test of groups of rats not receiving the compound, the basic source of the compound being rat brains, still another group of rats were tested in the same way, with controls as before, but with the use of the compound obtained from the brains of mice. A facilitation of learning of the same magnitude as that found in the said previous test animals occurred.

It will be understood that the detailed product recovery steps recited above under the heading "Method of Preparation", include many steps with the object of recovering the highest possible yield and except for that purpose are not to be considered essential, as indicated by the following claim 3.

Having described my invention, what I claim and desire to secure by Letters Patent, is as follows:

1. A method of obtaining a composition adapted for use by injection into the animal organism for topical action upon the animal brain to produce synthesis of brain components involved in the learning process, comprising deoxyribonucleic acid which contains 5 Hydroxymethylcytosine, with substantial inhibiting of enzymes and chemical degradents, said method comprising the steps of homogenizing an animal brain in a solution of sodium bromide, potassium citrate, sodium arsenite, sodium deoxycholate and glutathione, precipitating DNA with alcohol, transferring the resultant precipitate to the aforesaid solution form but omitting the sodium bromide and subjecting said precipitate to further homogenizing, followed by the consecutive additional steps, namely:

a. Transferring the said precipitated solids thus treated to a solution which is the same as that first stated but omitting the sodium bromide and the sodium deoxycholate and reducing concentration of glutathione; and stirring the solution in the presence of an active precipitant and thereby forming a white precipitant b. The white precipitant is dissolved in a solution of the same form as that stated in (a) together with lysozyme the latter having been purified by a water bath.

c. The white precipitate of deoxyribonucleic acid and lysozyme in its solvent is stirred, centrifuged, and the supernatent solution is discarded and the precipitated solids are washed with a solution composition as in (a) above and then dissolved in a solution the same as that stated above for hydrogenation but with lower sodium bromide concentration and precipitated with alcohol and by such action is formed a white precipitate of deoxyribonucleic acid, while the lysozyme is discarded; the precipitate then is transferred to a solution which is identical to that used after the last named homogenation step, dissolved and further purified by treatment with chloroform-isomethyl alcohol mixture; then the solution of deoxyribonucleic acid is precipitated with alcohol, dissolved in dilute citrate, physiological sodium chloridr- chloride - 0.14M, and dilute glutathione. Finally the composition is precipitated with alcohol from said solution.

2. A composition adapted for use by injection into the animal organism for topical action upon the animal brain, produced by the steps specified in claim 1, comprising deoxyribonecluic acid containing 5-hydroxymethylcytosine with substantial inhibition of enzymes and chemical degradents, and effective to produce synthesis of brain components involved in the learning process.

* * * * *